(12) United States Patent
Albert et al.

(10) Patent No.: US 10,364,260 B2
(45) Date of Patent: Jul. 30, 2019

(54) PROCESS FOR PREPARING TRIS[3-(ALKOXYSILYL)PROPYL] ISOCYANURATES

(71) Applicant: Evonik Degussa GmbH, Essen (DE)

(72) Inventors: Philipp Albert, Rheinfelden (DE); Eckhard Just, Rheinfelden (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 15/915,138

(22) Filed: Mar. 8, 2018

(65) Prior Publication Data

US 2018/0258110 A1    Sep. 13, 2018

(30) Foreign Application Priority Data

Mar. 8, 2017   (EP) .................................... 17159890

(51) Int. Cl.
 *C07D 251/34* (2006.01)
 *C07F 7/18* (2006.01)
(52) U.S. Cl.
 CPC .............. *C07F 7/1804* (2013.01); *C07F 7/18* (2013.01); *C07F 7/1876* (2013.01); *Y02P 20/588* (2015.11)
(58) Field of Classification Search
 CPC ..................................................... C07D 251/34
 USPC ........................................................ 544/221
 See application file for complete search history.

(56) References Cited

U.S. PATENT DOCUMENTS

| | | | |
|---|---|---|---|
| 3,517,001 A | 6/1970 | Berger | |
| 3,607,901 A | 9/1971 | Berger | |
| 3,821,218 A | 6/1974 | Berger | |
| 5,986,124 A | 11/1999 | Tachikawa et al. | |
| 6,048,994 A | 4/2000 | Tachikawa et al. | |
| 9,951,091 B2 * | 4/2018 | Albert .................. | C07D 251/34 |
| 10,125,156 B2 | 11/2018 | Albert et al. | |
| 2013/0158281 A1 | 6/2013 | Weller et al. | |
| 2018/0258109 A1 | 9/2018 | Albert et al. | |
| 2019/0048032 A1 | 2/2019 | Albert et al. | |

FOREIGN PATENT DOCUMENTS

| | | |
|---|---|---|
| CA | 943 544 | 3/1974 |
| CN | 101 805 366 | 8/2010 |
| CS | 195 549 | 2/1980 |
| EP | 0 583 581 | 2/1994 |
| EP | 0 587 462 | 3/1994 |
| EP | 0 856 517 | 8/1998 |
| EP | 1 150 346 | 10/2001 |
| EP | 1 885 731 | 11/2009 |
| EP | 1 869 058 | 12/2009 |
| JP | 4266400 | 5/2009 |
| WO | 2006/113182 | 10/2006 |

OTHER PUBLICATIONS

U.S. Appl. No. 15/915,126, filed Mar. 8, 2018, Philipp Albert.
U.S. Appl. No. 15/984,139, filed May 18, 2018, Wiebke Stache.
U.S. Appl. No. 16/159,763, filed Mar. 8, 2018, 2019/0048032, Albert et al.
Search Report issued in European Application No. 17159890.7 dated Apr. 20, 2017 (8 pp.).
Yoshino et al., "Synthesis of bone formation deriving biosilanes," Colloids and Surfaces B: Biointerfaces, 66, pp. 71-76, 2008.

* cited by examiner

*Primary Examiner* — Kahsay Habte
(74) *Attorney, Agent, or Firm* — Grüneberg and Myers PLLC

(57) ABSTRACT

The present invention relates to a process for preparing a tris[3-(alkoxysilyl)propyl] isocyanurate from the group of tris-[3-(trialkoxysilyl)propyl] isocyanurate, tris[3-(alkyldialkoxysilyl)propyl] isocyanurate and tris[3-(dialkylalkoxysilyl)propyl] isocyanurate by hydrosilylation, by
  in step A initially charging a mixture comprising at least one hydroalkoxysilane from the group of hydrotrialkoxysilane, hydroalkyldialkoxysilane, hydrodialkylalkoxysilane [called H-silane(s) for short], at least one carboxylic acid and a Pt catalyst, heating the mixture to a temperature of 50 to 140° C.,
  in step B adding a mixture of 1,3,5-triallyl-1,3,5-triazine-2,4,6(1H,3H,5H)-trione and at least one alcohol to the mixture from step A while mixing,
  in step C leaving the mixture from step B to react while mixing and
  in step D working up the product mixture thus obtained.

19 Claims, No Drawings

PROCESS FOR PREPARING TRIS[3-(ALKOXYSILYL)PROPYL] ISOCYANURATES

The present invention relates to a particularly economically viable process for preparing tris[3-(trialkoxysilyl)propyl] isocyanurate, tris[3-(alkyldialkoxysilyl)propyl] isocyanurate and tris[3-(diakylalkoxysilyl)propyl] isocyanurate (also referred to collectively hereinafter as tris[3-(alkoxysilyl)propyl] isocyanurates for short), wherein 1,3,5-triallyl-1,3,5-triazine-2,4,6(1H,3H,5H)-trione is hydrosilylated with a hydrotrialkoxysilane, hydroalkyldialkoxysilane or hydrodialkylalkoxysilane in the presence of a Pt catalyst, a carboxylic acid and a further cocatalyst.

Tris[3-(alkoxysilyl)propyl] isocyanurates are silanes that can be used as crosslinkers. By virtue of the three alkoxysilyl groups, of which each alkoxysilyl group after hydrolysis can enter into one, two or three chemical bonds, three up to nine chemical bonds are theoretically possible. By virtue of these significant crosslinking opportunities, tris[3-(alkoxysilyl)propyl] isocyanurates are of interest for various applications. A further advantage of tris[3-(alkoxysilyl)propyl] isocyanurates is the high thermal stability that enables use in the high-temperature range. Tris[3-(alkoxysilyl)propyl] isocyanurates can therefore be used advantageously as crosslinker, for example, in paint and rubber formulations and as adhesion promoter in paints and adhesives in a wide variety of different industries. The high crosslinking density additionally allows production of scratch-resistant coatings and barrier layers.

JP4266400B describes the preparation of an aromatic silane compound by hydrosilylation of an aromatic vinyl compound. The catalyst used is a platinum complex in the presence of a carboxylic acid.

U.S. Pat. No. 5,986,124 relates to a process for preparing a silane compound by hydrosilylation of a carbon double bond by means of a trialkoxyhydrosilane in the presence of a platinum catalyst and a carboxylic acid. Through the use of platinum catalysts together with carboxylic acids, it is possible to achieve a conversion of about 80% in the hydrosilylation, but crude products thus obtained still include a considerable proportion of impurities and/or by-products.

EP 0587462 describes a composition composed of an unsaturated polyorganosiloxane, an organohydropolysiloxane, an acid, a platinum compound and additives, wherein the components are emulsified in water and used for surface release treatment. The crosslinking is effected via hydrosilylation in the course of heating.

EP 0856517 discloses a process for hydrosilylation of an unsaturated compound in the presence of a metal compound of transition groups 8 to 10 of the Periodic Table of the Elements. The hydrosilylation is conducted in the presence of an accelerator.

EP 1869058/WO 2006/113182 presents a process for preparing tris[3-(trialkoxysilyl)propyl] isocyanurate. The preparation proceeds via the cracking of silyl organocarbamate in the presence of a catalytic amount of a carboxylate salt.

EP 0583581 teaches the preparation of a silyl organocarbamate from an aminosilane. The silyl organocarbamate is subsequently converted to the silyl isocyanurate in the presence of a "cracking catalyst".

EP 1585731 discloses a process for preparing isocyanatosilanes and silyl isocyanurate. The synthesis starts with a silyl organocarbamate. By catalytic cracking, the isocyanatosilane is released, and the conversion of the isocyanatosilane to the silyl isocyanurate is effected in a trimerization reaction zone.

CA 943544 describes the preparation of a silyl organoisocyanurate from a haloalkylsilane and a metal cyanate in the presence of a solvent. The solvent and the salt formed are removed after the reaction.

U.S. Pat. No. 3,607,901 relates to the preparation of isocyanatosilanes and isocyanuratosilanes proceeding from chloroalkyltrialkoxysilanes and a metal cyanate.

U.S. Pat. No. 3,517,001 teaches, inter alia, the preparation of 1,3,5-tris(trimethoxysilylpropyl) isocyanurate by hydrosilylation of 1,3,5-tris(allyl isocyanurates) with trimethoxysilane in the presence of hexachloroplatinic acid. The yield is reported as 40%.

U.S. Pat. No. 3,821,218 describes the preparation of 1,3,5-tris(trimethoxysilylpropyl) isocyanurate proceeding from chloropropyltrimethoxysilane and potassium cyanate in DMF as solvent.

US 2013/0158281 discloses a process for hydrosilylation of an unsaturated compound with a silyl hydride. The catalysts used are Fe complexes, Ni complexes, Mn complexes or Co complexes.

CN 101805366 describes the preparation of 1,3,5-tris(trimethoxysilylpropyl) isocyanurate by cyclocondensation of isocyanatopropyltrimethoxysilane.

CS 195549 relates to the hydrosilylation of vinylcyclohexane with hydrosilanes. In example 4, vinylcyclohexane is hydrolysed by means of triethoxysilane in the presence of platinic acid and trifluoroacetic acid.

The problem addressed by the present invention was that of providing a process for preparing tris[3-(alkoxysilyl)propyl] isocyanurates, i.e. from the group of tris[3-(trialkoxysilyl)propyl] isocyanurate, tris[3-(alkyldialkoxysilyl)propyl] isocyanurate and tris[3-dialkylalkoxysilyl)propyl] isocyanurate, where alkyl is especially—but not exclusively—methyl or ethyl and alkoxy is methoxy or ethoxy, in which a Pt catalyst is used in conjunction with a carboxylic acid and the disadvantages detailed above are reduced if possible via a controlled reaction regime, specific feed ratios and/or further additions. Furthermore, another aim was, if possible, to conduct the process with a minimum concentration of costly platinum and without the separate addition of an aliphatic or aromatic solvent and to increase the yield of target product. It was also desirable to keep the content of carboxylic acid remaining in the target product to a minimum.

The problem is solved according to the present claims.

It has been found that, surprisingly, significantly better yields of target product, i.e. a tris[3-(alkoxysilyl)propyl] isocyanurate, are achieved when the hydrosilylation is performed by
  in step A initially charging a mixture comprising at least one hydroalkoxysilane from the group of hydrotrialkoxysilane, hydroalkyldialkoxysilane, hydrodialkylalkoxysilane [called H-silane(s) for short], at least one carboxylic acid and a Pt catalyst, heating the mixture to a temperature of 50 to 140° C.,
  in step B adding a mixture of 1,3,5-triallyl-1,3,5-triazine-2,4,6(1H,3H,5H)-trione and at least one alcohol to the mixture from step A while mixing,
  in step C leaving the mixture from step B to react while mixing and
  in step D working up the product mixture thus obtained and so the reaction and the selectivity and hence the yield of the hydrosilylation is markedly promoted.

It has been found here to be particularly advantageous that the present process is preferably conducted with a homogeneous platinum(0) complex catalyst, especially a "Karstedt catalyst", a "Speier catalyst", hexachloroplatinum(IV) acid or a supported, i.e. heterogeneous, Pt catalyst, for example Pt on activated carbon. In addition, a "Karstedt catalyst" is preferably used in the form of a platinum(0) complex catalyst solution, especially dissolved in xylene or toluene.

The present procedure also makes it possible to reduce the content of Pt catalyst/the Pt loss, and hence to save costly Pt. Moreover, it has been found to be particularly advantageous in the present process to use a carboxylic acid from the group of benzoic acid, 3,5-di-tert-butylbenzoic acid, 3,5-di-tert-butyl-4-hydroxybenzoic acid, 2,2-dimethylpropionic acid, propionic acid and/or acetic acid.

A product mixture obtained by the present process is suitably worked up by distillation, optionally under reduced pressure, and the desired (target) product is obtained.

In the case of use of a heterogeneous catalyst, the latter can suitably be separated from the product mixture prior to the distillation, for example by filtration or centrifugation, and this Pt catalyst thus recovered can advantageously be recycled into the process.

For instance, the target product is obtained as bottom product in the distillation conducted after the reaction and, if necessary, after the removal, of a heterogeneous catalyst the target product is not distilled over in the distillative workup and is obtained as a colourless bottom product.

In the present process, the double bonds of the olefin component used here can advantageously be virtually completely hydrosilylated, advantageously giving rise to only a very low level of by-products.

Furthermore, the present process, i.e. that according to the invention, can advantageously be conducted without separate addition of an aliphatic or aromatic hydrocarbon as solvent or diluent, and with only a small proportion of the carboxylic acid (co-)catalyst component which remains in the target product.

The present invention thus provides a process for preparing a tris[3-(alkoxysilyl)propyl] isocyanurate from the group of tris[3-(trialkoxysilyl)propyl] isocyanurate, tris[3-(alkyldialkoxysilyl)propyl] isocyanurate and tris[3-(dialkylalkoxysilyl)propyl] isocyanurate by hydrosilylation, by in step A initially charging a mixture comprising at least one hydroalkoxysilane from the group of hydrotrialkoxysilane, hydroalkyldialkoxysilane, hydrodialkylalkoxysilane [called H-silane(s) for short], at least one carboxylic acid and a Pt catalyst, heating the mixture to a temperature of 50 to 140° C., in step B adding a mixture of 1,3,5-triallyl-1,3,5-triazine-2,4,6(1H,3H,5H)-trione and at least one alcohol to the mixture from step A while mixing, in step C leaving the mixture from step B to react while mixing and in step D working up the product mixture thus obtained.

In the process according to the invention, H-silane is advantageously used relative to olefin component in a molar ratio of 1:0.1 to 1, preferably of 1:0.2 to 0.4, especially—to give just a few of the possible intermediate values here that will be clear or derivable for the person skilled in the art from the figures above and the present figures, in a representative manner and by way of example—1:0.13, 1:0.15, 1:0.18, 1:0.23, 1:0.25, 1:0.28, 1:0.3, 1:0.33, 1:0.35, 1:0.38.

The H-silane used here is preferably hydrotrimethoxysilane (TMOS), hydrotriethoxysilane (TEOS), methyldiethoxysilane (DEMS), methyldimethoxysilane (DMMS), dimethylethoxysilane (DMES) and/or dimethylmethoxysilane (MDMS).

Moreover, in the process according to the invention, the olefin component used is 1,3,5-triallyl-1,3,5-triazine-2,4,6 (1H,3H,5H)-trione.

Advantageously, in the process according to the invention, it is preferable to use H-silane relative alcohol in a molar ratio of 1:0.005 to 0.3, preferably 0.01 to 0.2, preferably 1:0.02 to 0.18, more preferably 1:0.03 to 0.15, even more preferably 1:0.04 to 0.1, especially 1:0.05 to 0.06. Preferably, for this purpose, at least one alcohol is selected from the group of the C1-C10 alcohols, more preferably at least one from the group of tert-butanol, ethanol, methanol, benzyl alcohol and diglycol monomethyl ether.

Moreover, in the process according to the invention, H-silane is advantageously used relative to Pt in a molar ratio of $1:1\times10^{-4}$ to $1\times10^{-9}$, preferably $1:1\times10^{-5}$ to $1\times10^{-5}$, especially of $1:1\times10^{-5}$ to $9\times10^{-6}$.

The Pt catalyst used here is suitably a heterogeneous Pt catalyst, preferably Pt applied to a solid catalyst support, especially Pt on activated carbon, or a homogeneous Pt catalyst, preferably a Pt complex catalyst, such as hexachloroplatinum(IV) acid, also called "Speier catalyst", especially hexachloroplatinum(IV) acid dissolved in acetone, preferably a Pt(0) complex catalyst, more preferably a "Karstedt catalyst", even more preferably a platinum(0)-1,3-divinyl-1,1,3,3-tetramethyldisiloxane complex, especially a "Karstedt catalyst" in xylene or toluene with a Pt(0) content of 0.5% to 5% by weight. Such a solution generally contains a platinum(0)-1,3-divinyl-1,1,3,3-tetramethyldisiloxane complex dissolved in xylene or toluene, and a solution used in accordance with the invention is advantageously used in dilute form and preferably contains a Pt content of 0.5% to 5% by weight. Thus, in the process according to the invention, it is advantageous to use a Pt catalyst from the group of "Karstedt catalyst", especially a "Karstedt catalyst" solution, preferably platinum(0)-1,3-divinyl-1,1,3,3-tetramethyldisiloxane complex in xylene or toluene with a Pt(0) content of 0.5% to 5% by weight, hexachloroplatinum(IV) acid, preferably "Speier catalyst", especially hexachloroplatinum(IV) acid dissolved in acetone, or Pt supported on activated carbon.

Further, in the process according to the invention, H-silane is preferably used relative to carboxylic acid in a molar ratio of $1:1\times10^{-3}$ to $30\times10^{-3}$, more preferably $1:1\times10^{-3}$ to $10\times10^{-3}$, especially of $1:2\times10^{-3}$ to $8\times10^{-3}$.

For this purpose, the carboxylic acid is preferably selected from the group of benzoic acid, 3,5-di-tert-butylbenzoic acid, 3,5-di-tert-butyl-4-hydroxybenzoic acid, 2,2-dimethylpropionic acid, propionic acid, acetic acid.

It is thus possible, in general, to execute the process according to the invention—with all its possible combinations of the features detailed in the present description—as follows:

For the performance of the hydrosilylation according to the invention for preparation of a tris[3-(alkoxysilyl)propyl] isocyanurate, a stirred reactor with metering apparatus, heating/cooling apparatus, reflux apparatus and distillation apparatus, suitably under protective gas, for example nitrogen, in step A is initially charged with a mixture comprising at least one hydroalkoxysilane from the group of hydrotrialkoxysilane, hydroalkyldialkoxysilane, hydrodialkylalkoxysilane [called H-silane(s) for short], at least one carboxylic acid, preferably benzoic acid, 3,5-di-tert-butylbenzoic acid, 3,5-di-tert-butyl-4-hydroxybenzoic acid, 2,2-dimethylpropionic acid, propionic acid and/or acetic acid, and a Pt catalyst, suitably a "Speier catalyst", preferably hexachloroplatinum(IV) acid in acetone or hexachloroplatinum(IV) acid hexahydrate dissolved in acetone or a "Karstedt catalyst", the latter preferably being used in the form of a platinum(0) complex catalyst solution, or Pt on activated carbon, and the mixture is heated to a temperature of 40 to 140° C., preferably to a temperature of 50 to 120° C., in step B a mixture of 1,3,5-triallyl-1,3,5-triazine-2,4,6 (1H,3H,5H)-trione and at least one alcohol is added to the mixture from step A, preferably under temperature control and over 1 to 10 or more hours, in step C the mixture from step B is left to react further while mixing, suitably at a temperature of 60 to 100° C., especially over 0.5 to 2 hours; metering and reaction times mentioned above are guideline values and may indeed be dependent on the batch size and the reactor design, in the subsequent step D the product mixture thus obtained is worked up.

Thus, in present processes, the respective feedstocks are preferably used in a well-defined molar ratio:

H-silane to olefin component in a molar ratio of 1:0.1 to 1

H-silane to alcohol in a molar ratio of 1:0.005 to 0.3

H-silane to Pt in a molar ratio of $1:1\times10^{-4}$ to $1\times10^{-9}$

H-silane to carboxylic add in a molar ratio of $1:1\times10^{-3}$ to $30\times10^{-3}$ In addition, the "Karstedt catalyst" solution used is preferably prepared from a conventional "Karstedt catalyst concentrate" (platinum(0)-1,3-divinyl-1,1,3,3-tetramethyldisiloxane complex, platinum content: 20.37% by weight) (also referred to as "Karstedt concentrate" hereinafter for short), the concentrate preferably being adjusted to a Pt content of 0.5% to 5% by weight by the addition of xylene or toluene.

A product mixture thus obtained is a suitably worked up by distillation to obtain the desired (target) product. For this purpose, the distillation is preferably conducted commencing at 45° C. to 150° C. and a reduced pressure (vacuum distillation at less than 1 bar and falling, especially not more than 0.1 bar), wherein low boilers that are present in particular, for example carboxylic acid, alcohol, excess H-silane and any olefin component still present are removed from the product mixture. If a heterogeneous Pt catalyst is used for performance of the process according to the invention, the heterogeneous Pt catalyst can be separated from the product mixture obtained after the reaction in the course of the product workup, i.e. prior to the distillation step, for example by filtration or centrifugation, and advantageously be recycled back into the process.

It is thus advantageously possible to prepare tris[3-(alkoxysilyl)propyl] isocyanurates obtainable in accordance with the invention in comparatively high yield and selectivity, i.e. with only small proportions of by-products, even on the industrial scale in a simple and economically viable manner.

The examples which follow provide additional illustration of the present invention without restricting the subject-matter:

EXAMPLES

Analytical Methods:
NMR Measurements:
Instrument: Bruker
Frequency: 500.1 MHz ($^1$H NMR)
Scans: 32
Temperature: 303 K
Solvent: CDCl$_3$
Standard: 0.5% TMS (tetramethylsilane)

Explanations are given below with regard to naming of target product and by-products formed in the synthesis with respect to the present $^1$H NMR evaluations using the example of the structural formula of a tris[3-(trialkoxysilyl) propyl] isocyanurate. The determinations of selectivities with respect to tris[3-(methyldialkoxysilyl)propyl] isocyanurate and tris[3-(dimethylalkoxysilyl)propyl] isocyanurate were conducted analogously and are listed in the tables for Examples 6 and 7.

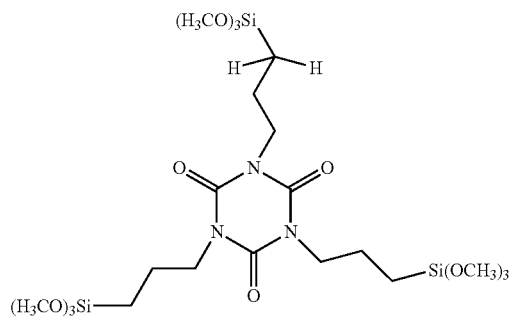

in the target product: functional group S1 (Si—CH$_2$—)

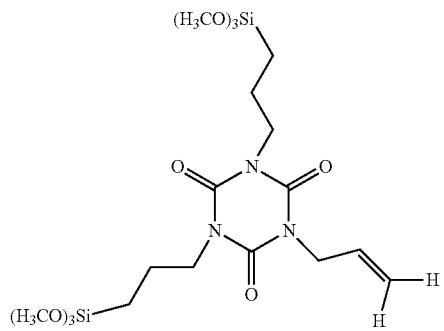

in the so-called allyl derivative: functional group A1

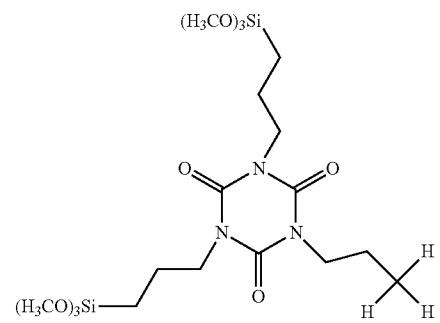

in the so-called propyl derivative: functional group P1

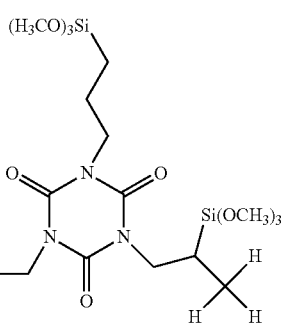

in the so-called isopropyl derivative: functional group I1

The experiments were evaluated using the product formed in the hydrosilylation of the 1,3,5-triallyl-1,3,5-triazine-2,4,6(1H,3H,5H)-trione. The more allylic double bonds were converted to the target product and the fewer secondary components were formed, the better the product quality and the performance/selectivity of the catalyst system. A high selectivity is very important because the secondary components can be removed by distillation from the target product only with a very high level of complexity, if at all.

The 1H NMR spectra were evaluated using the hydrogen atoms included in the structural formula drawings. The hydrosilylation gives rise to Si—CH$_2$— groups that are characteristic of the target product. The Si—CH$_2$— groups were identified with S1, the allylic groups (C=CH$_2$— group) with A1, the propyl group (C$_3$H$_7$— group) with P1 and the isopropyl group with I1. The evaluation of the 1H NMR spectra and the calculation of the functional groups was shown after each experiment in the tables. The evaluated signals from the $^1$H NMR form triplets (t) for the S1 and P1 group, double doublets (dd) for the A1 group, and doublets (d) for the I1 group.

Chemicals Used:

"Karstedt concentrate" (platinum(0) 1,3-divinyl-1,1,3,3-tetramethyldisiloxane complex, platinum content: 20.37% by weight), HERAEUS Acetone, pure, LABC Labortechnik Hexachloroplatinum(IV) acid hexahydrate, platinum content 40% by weight, HERAEUS Platinum-activated carbon, hydrogenation catalyst, platinum content 10% by weight, MERCK Benzyl alcohol, puriss, SIGMA ALDRICH Diethylene glycol monomethyl ether >98% by weight, MERCK Xylene Technical, VWR Chemicals Dynasylan® TMOS (trimethoxysilane), EVONIK Industries Dynasylan® TEOS-H (triethoxysilane), EVONIK Industries Dynasylan® DEMS (methyldiethoxysilane), EVONIK Industries Dynasylan® DMES (dimethylethoxysilane), EVONIK Industries TIACROS® (1,3,5-triallyl-1,3,5-triazine-2,4,6(1H,3H,5H)-trione), EVONIK Industries Benzoic acid ≥99.5% by weight, ROTH 3,5-Di-tert-butylbenzoic acid >98.0% by weight, TOKYO CHEMICAL INDUSTRY 3,5-Di-tert-butyl-4-hydroxybenzoic acid, >98.0% by weight, TOKYO CHEMICAL INDUSTRY Acetic acid, ≥99% by weight, SIGMA-ALDRICH Methanol ≥99.5% by weight, MERCK Ethanol ≥99.8% by weight, ROTH tert-Butanol, ≥99.0% by weight (for synthesis), ROTH Chloroform-d1 (CDCl$_3$)+0.5% by weight of TMS, DEUTERO Benzene-d6, DEUTERO Tetramethylsilane, DEUTERO Preparation of "Karstedt-Catalyst" No. 1 with Platinum Content 2% by Weight in Xylene:

In a 0.2 l glass bottle, 9.8 g of "Karstedt concentrate" (platinum(0) 1,3-divinyl-1,1,3,3-tetramethyldisiloxane complex, platinum content 20.37%) were mixed with 90.2 g of xylene.

Preparation of "Karstedt-Catalyst" No. 2 with Platinum Content 2% by Weight in Toluene:

In a 0.2 l glass bottle, 9.8 g of "Karstedt concentrate" (platinum(0) 1,3-divinyl-1,1,3,3-tetramethyldisiloxane complex, platinum content 20.37% by weight) were mixed with 90.2 g of toluene.

Preparation of "Karstedt-Catalyst" No. 3 with Platinum Content 0.4% by Weight:

In a 0.1 l glass bottle, 196.4 mg of "Karstedt concentrate" (platinum(0) 1,3-divinyl-1,1,3,3-tetramethyldisiloxane complex, platinum content 20.37% by weight) were mixed with 9.8 g of toluene.

Preparation of Catalyst 4 from Hexachloroplatinum(IV) Acid Hexahydrate Solution in Acetone with Pt Content 2.34% by Weight:

In a 12 l plastic vessel, 530 g of H$_2$PtCl$_6$x6H$_2$O were dissolved in 9.8 l of acetone. The catalyst solution thus prepared was used after maturing for 8 weeks.

COMMENT ON THE COMPARATIVE EXAMPLES WHICH FOLLOW

The synthesis in ampoules described in U.S. Pat. No. 5,986,124 cannot be conducted on the industrial scale. In order that the experiments can be better compared with the inventive examples, the experiments were conducted in a stirred tank or flask. Furthermore, in the examples in U.S. Pat. No. 5,986,124, different unsaturated compounds were used, and so a direct comparison with the present invention would not be possible; thus, TAICROS® was used in the comparative examples which follow.

Comparative Example 1: Based on Example 1 from U.S. Pat. No. 5,986,124

0.2003 mol (24.5 g) of Dynasylan® TMOS, 0.1 ml of Catalyst No. 1, a further 40.0 g of toluene as additional solvent/diluent, 0.0665 mol (16.8 g) of TAICROS® and 0.4 ml of acetic acid were initially charged in a 0.25 l stirred apparatus with jacketed coil condenser and stirred in an oil bath heated to 53-55° C. for 2.5 hours. This gave 79.9 g of incompletely converted and colourless bottom product. The volatile components were not removed.

Evaluation of the $^1$H NMR spectrum with regard to Comparative Example 1:

| Solvent: CDCl$_3$ + 0.5% TMS | Signal at [ppm] | Integral I | N Number of protons | I/N | % (mol) |
|---|---|---|---|---|---|
| S1 | 0.64 | 100.00 | 2 | 50.00 | 45.8 |
| A1 | 5.27 | 117.28 | 2 | 58.64 | 53.7 |
| P1 | 0.93 | 0.81 | 3 | 0.27 | 0.3 |
| I1 | 1.00 | 0.61 | 3 | 0.20 | 0.2 |

Result: 45.8% of the allyl groups were converted by hydrosilylation to trimethoxysilylalkyl groups (cf. S1). 53.7% of the allyl groups (A1) have not been converted, and 0.3% propyl groups (P1) and 0.2% isopropyl groups (I1) that contaminate the product have formed. The reaction is incomplete.

Comparative Example 2: Based on Example 1 from U.S. Pat. No. 5,986,124

0.2003 mol (32.9 g) of Dynasylan® TEOS-H, 0.1 ml of Catalyst No. 3, a further 40.0 g of toluene as additional solvent/diluent, 0.0665 mol (16.6 g) of TAICROS® and 0.4 ml of acetic acid were initially charged in a 0.25 l stirred apparatus with reflux condenser and stirred in an oil bath heated to 50-57° C. for 2.5 hours. This gave 88.2 g of incompletely converted and colourless bottom product. The volatile components were not removed.

Evaluation of the $^1$H NMR spectrum with regard to Comparative Example 2:

| Solvent: CDCl$_3$ + 0.5% TMS | Signal at [ppm] | Integral I | N Number of protons | I/N | % (mol) |
| --- | --- | --- | --- | --- | --- |
| S1 | 0.64 | 100.00 | 2 | 50.00 | 86.2 |
| A1 | 5.26 | 14.59 | 2 | 7.30 | 12.6 |
| P1 | 0.94 | 0.33 | 3 | 0.33 | 0.6 |
| I1 | 1.06 | 0.35 | 3 | 0.35 | 0.6 |

Result: 86.2% of the allyl groups were converted by hydrosilylation to trimethoxysilylalkyl groups (cf. S1). 12.6% of the allyl groups (A1) have not been converted, and 0.6% propyl groups (P1) and 0.6% isopropyl groups (I1) that contaminate the product have formed. The reaction is incomplete.

Comparative Example 3: With Acetic Acid Only, No Addition of Alcohol 1.2 mol of DYNASYLAN® TMOS and 0.2 g of Catalyst No. 1 (corresponding to 0.0205 mmol of Pt) were initially charged in a 0.5 l stirred apparatus with reflux condenser, metering apparatus. At a temperature of 76-91° C., a mixture consisting of 0.33 mol of TAICROS® and 6.77 mmol of acetic acid was metered in within 1 h. Thereafter, the mixture was left to react further at about 87-92° C. for about 1 further hour. Subsequently, 55.0 g of low boilers were removed at 90-120° C. and a pressure of <0.1 mbar. This gave 170.7 g of incompletely converted, colourless bottom product.

Evaluation of the $^1$H NMR spectrum with regard to Comparative Example 3:

| Solvent: CDCl$_3$ + 0.5% TMS | Signal at [ppm] | Integral I | N Number of protons | I/N | % (mol) |
| --- | --- | --- | --- | --- | --- |
| S1 | 0.66 | 100.00 | 2 | 50.00 | 73.8 |
| A1 | 5.25 | 34.79 | 2 | 17.40 | 25.7 |
| P1 | 0.94 | 0.61 | 3 | 0.20 | 0.3 |
| I1 | 1.01 | 0.43 | 3 | 0.14 | 0.2 |

Result: 73.8% of the allyl groups were converted by hydrosilylation to trimethoxysilylalkyl groups (cf. S1). 25.7% of the allyl groups (A1) have not been converted, and 0.3% propyl groups (P1) and 0.2% isopropyl groups (I1) that contaminate the product have formed. The reaction is incomplete.

Comparative Example 4

1.2 mol of Dynasylan® TMOS, 0.2 g of "Karstedt catalyst" (corresponding to 0.0205 mmol of Pt), 34.38 mmol of methanol and 6.55 mmol of benzoic acid were initially charged in a 0.5 l stirred apparatus with reflux condenser, metering apparatus. At a temperature of 73-82° C., 0.33 mol of TAICROS® was metered in within 1 hour. Thereafter, the mixture was left to react further at 81° C. for another 1 hour. Subsequently, 89.5 g of low boilers were removed at 35-127° C. and a pressure of <0.1 mbar. This gave 134.2 g of incompletely converted and colourless bottom product.

Evaluation of the $^1$H NMR spectrum from Comparative Example 4:

| Solvent: CDCl$_3$ + 0.5% TMS | Signal at [ppm] | Integral | N Number of protons | I/N | % (mol) |
| --- | --- | --- | --- | --- | --- |
| S1 | 0.66 | 100.00 | 2 | 50.00 | 42.5 |
| A1 | 5.25 | 134.10 | 2 | 67.05 | 57.0 |
| P1 | 0.94 | 1.24 | 3 | 0.41 | 0.4 |
| I1 | 1.01 | 0.36 | 3 | 0.12 | 0.1 |

Result: 42.5% of the allyl groups were converted by hydrosilylation with TMOS to trimethoxysilylalkyl groups (cf. S1). 57.0% of the allyl groups (A1) were not converted. 0.4% propyl groups (P1) and 0.1% isopropyl groups (I1) that contaminate the product were formed. The conversion of the allyl groups is incomplete, and only a low level of by-products is formed.

Comparative Example 5

1.2 mol of Dynasylan® TMOS, 0.2 g of "Karstedt catalyst" (corresponding to 0.0205 mmol of Pt) and 34.38 mmol of methanol were initially charged in a 0.5 l stirred apparatus with reflux condenser, metering apparatus. At a temperature of 70-87° C., a mixture consisting of 0.33 mol of TAICROS® and 6.55 mmol of benzoic acid was metered in within 1 hour. Thereafter, the mixture was left to react further at 81° C. for another 1 hour. Subsequently, 41.5 g of low boilers were removed at 61-121° C. and a pressure of <0.1 mbar. This gave 183.0 g of incompletely converted and colourless bottom product.

Evaluation of the 1H NMR spectrum from Comparative Example 5:

| Solvent: CDCl$_3$ + 0.5% TMS | Signal at [ppm] | Integral | N Number of protons | I/N | % (mol) |
| --- | --- | --- | --- | --- | --- |
| S1 | 0.66 | 100.0 | 2 | 50.00 | 81.5 |
| A1 | 5.25 | 21.75 | 2 | 10.87 | 17.7 |
| P1 | 0.94 | 1.09 | 3 | 0.36 | 0.6 |
| I1 | 1.01 | 0.38 | 3 | 0.13 | 0.2 |

Result: 81.5% of the allyl groups were converted by hydrosilylation with TMOS to trimethoxysilylalkyl groups (cf. S1). 17.7% of the allyl groups (A1) were not converted. 0.6% propyl groups (P1) and 0.2% isopropyl groups (I1) that contaminate the product were formed. The conversion of the allyl groups is incomplete, and only a low level of by-products is formed.

Comparative Example 6

0.33 mol (83.1 g) of TAICROS®, 0.2 g of Catalyst No. 1 (corresponding to 0.0205 mmol of Pt) and 6.79 mmol (1.7 g) of 3,5-di-tert-butyl-4-hydroxybenzoic acid were initially charged in a 0.5 l stirred apparatus with reflux condenser, metering apparatus. At a temperature of 91-111° C., 1.2 mol (146.6 g) of Dynasylan® TMOS were supposed to be metered in. The hydrosilylation is highly exothermic and, after metered addition of 18 g of Dynasylan® TMOS, the temperature had already risen from 91 to 97° C. within 9 minutes. Once a further 72 g of Dynasylan® TMOS had been metered in within 27 minutes and the temperature had risen to 108° C., it was not possible to detect any exothermicity in the course of further addition of Dynasylan® TMOS. The reaction mixture cooled down from 108 to 89° C. within a few minutes. The experiment was therefore stopped after metered addition of a total of 90 g of Dynasylan® TMOS; in other words, the reaction stopped and the conversion in this procedure thus remained correspondingly incomplete. 68 g of Dynasylan® TMOS were not metered in.

Note:

The present comparative experiments for preparation of tris[3-(alkoxysilyl)propyl] isocyanurates by hydrosilylation of 1,3,5-triallyl-1,3,5-triazine-2,4,6(1H,3H,5H)-trione (TAICROS®) in the presence of a Pt catalyst system composed of Pt catalyst and carboxylic acid show that a comparatively low conversion of the double bond of well below 90 mol % is discovered when a mixture of H-silane, Pt catalyst, carboxylic acid and TAICROS® is used, heated and reacted as such H-silane and Pt catalyst are initially charged and heated and a mixture of TAICROS® and carboxylic acid is metered in H-silane, Pt catalyst and alcohol are initially charged and heated and a mixture of TAICROS® and carboxylic acid is metered in H-silane, Pt catalyst, carboxylic acid and alcohol are initially charged and heated and TAICROS® is metered in or TAICROS®, Pt catalyst and carboxylic acid are initially charged and heated and H-silane is metered in.

Example 1

1.2 mol of Dynasylan® TMOS, 0.2 g of "Karstedt catalyst" No. 1 (corresponding to 0.0205 mmol of Pt) and 6.55 mmol of benzoic acid were initially charged in a 0.5 l stirred apparatus with reflux condenser, metering apparatus. At a temperature of 71-82° C., a mixture consisting of 0.33 mol of TAICROS® and 50.0 mmol of methanol was metered in within 1 hour. Thereafter, the mixture was left to react further at 81° C. for another hour and then a $^1$H NMR spectrum of a sample of the liquid phase was measured.

Evaluation of the $^1$H NMR spectrum with regard to liquid phase sample of Example 1:

| Solvent: CDCl$_3$ + 0.5% TMS | Signal at [ppm] | Integral | N Number of protons | I/N | % (mol) |
|---|---|---|---|---|---|
| S1 | 0.66 | 100.0 | 2 | 50.00 | 98.1 |
| A1 | 5.25 | 0.05 | 2 | 0.03 | 0.1 |
| P1 | 0.94 | 2.20 | 3 | 0.73 | 1.4 |
| I1 | 1.01 | 0.57 | 3 | 0.19 | 0.4 |

Result: 98.1% of the allyl groups were converted by hydrosilylation with TMOS to trimethoxysilylalkyl groups. 0.1% of the allyl groups (A1) were not converted. 1.4% propyl groups (P1) and 0.4% isopropyl groups (I1) that contaminate the product were formed. The conversion of the allyl groups is not virtually complete, and only a low level of by-products is formed. Only traces of incompletely converted allyl groups are present.

The invention claimed is:

1. A process for preparing at least one tris[3-(alkoxysilyl)propyl] isocyanurate selected from the group consisting of tris[3-(trialkoxysilyl)propyl] isocyanurate, tris[3-(alkyldialkoxysilyl)propyl] isocyanurate and tris[3-(dialkylalkoxysilyl)propyl] isocyanurate by hydrosilylation, the process comprising:

(A) initially charging a mixture comprising at least one H-silane selected from the group consisting of hydrotrialkoxysilane, hydroalkyldialkoxysilane, and hydrodialkylalkoxysilane, with at least one carboxylic acid and a Pt catalyst, and heating the mixture to a temperature of 50 to 140° C., (B) adding a mixture of 1,3,5-triallyl-1,3,5-triazine-2,4,6 (1H,3H,5H)-trione and at least one alcohol to the mixture obtained in (A) while mixing, (C) leaving the mixture obtained in (B) to react while mixing and (D) working up the product mixture thus obtained.

2. The process according to claim 1, wherein a molar ratio of the at least one H-silane relative to alcohol is 1:0.005 to 0.3.

3. The process according to claim 1, wherein a molar ratio of the at least one H-silane relative to Pt is $1:1\times10^{-4}$ to $1\times10^{-9}$.

4. The process according to claim 1, wherein a molar ratio of the at least one H-silane relative to carboxylic acid is $1:1\times10^{-3}$ to $30\times10^{-3}$.

5. The process according to claim 1, wherein a molar ratio of the at least one H-silane relative to olefin component is 1:0.1 to 1.

6. The process according to claim 1, wherein the carboxylic acid is at least one selected from the group consisting of benzoic acid, propionic acid, 2,2-dimethylpropionic acid, 3,5-di-tert-butylbenzoic acid, 3,5-di-tert-butyl-4-hydroxybenzoic acid, and acetic acid.

7. The process according to claim 1, wherein the alcohol is at least one selected from the group consisting of C1-C10 alcohols.

8. The process according to claim 1, wherein the at least one H-silane is at least one selected from the group consisting of hydrotrimethoxysilane (TMOS), hydrotriethoxysilane (TEOS), methyldiethoxysilane (DEMS), methyldimethoxysilane (DMMS), dimethylethoxysilane (DMES) and dimethylmethoxysilane (MDMS).

9. The process according to claim 1, wherein the Pt catalyst is at least one catalyst selected from the group consisting of a Karstedt catalyst, hexachloroplatinum(IV) acid, and Pt applied to a solid catalyst support.

10. The process according to claim 1, wherein the alcohol is at least one selected from the group consisting of tert-butanol, ethanol, methanol, benzyl alcohol and diglycol monomethyl ether.

11. The process according to claim 1, wherein the Pt catalyst is a platinum(0)-1,3-divinyl-1,1,3,3-tetramethyldisiloxane complex in the form of a Karstedt catalyst in xylene or toluene with a Pt(0) content of 0.5% to 5% by weight, hexachloroplatinum(IV) acid dissolved in acetone, or Pt supported on activated carbon.

12. The process according to claim 1, wherein the Pt catalyst is a platinum(0)-1,3-divinyl-1,1,3,3-tetramethyldisiloxane complex in the form of a Karstedt catalyst in xylene or toluene with a Pt(0) content of 0.5% to 5% by weight.

13. The process according to claim 1, wherein the process does not comprise a separate addition of an aliphatic or aromatic hydrocarbon as solvent or diluent.

14. The process according to claim 1, wherein at least 90 mol % of allyl groups in the 1,3,5-triallyl-1,3,5-triazine-2,4,6(1H,3H,5H)-trione are converted by hydrosilylation to 3-(alkoxysilyl)propyl groups.

15. The process according to claim 1, further comprising:
separating the Pt catalyst from the product mixture obtained in (C) prior to (D) working up the product mixture, thereby obtaining a separated Pt catalyst, and recycling the separated Pt catalyst.

16. The process according to claim 1, wherein (D) working up the product mixture comprises distillation at a temperature of from 45° C. to 150° C. at a pressure of less than 1 bar, thereby removing at least one selected from the group consisting of carboxylic acid, alcohol, H-silane, and olefin.

17. The process according to claim 1, wherein said at least one tris[3-(alkoxysilyl)propyl] isocyanurate is tris[3-(trialkoxysilyl)propyl] isocyanurate.

18. The process according to claim 1, wherein said tris[3-(trialkoxysilyl)propyl] isocyanurate is tris[3-(trimethoxysilyl)propyl] isocyanurate.

19. The process according to claim 1, wherein said tris[3-(trialkoxysilyl)propyl] isocyanurate is tris[3-(triethoxysilyl)propyl] isocyanurate.

* * * * *